(12) United States Patent
Kim et al.

(10) Patent No.: US 11,554,146 B2
(45) Date of Patent: Jan. 17, 2023

(54) LACTIC ACID BACTERIA AND USE THEREOF

(71) Applicants: UNIVERSITY-INDUSTRY COOPERATION GROUP OF KYUNG HEE UNIVERSITY, Gyeonggi-do (KR); NAVIPHARM CO. LTD, Gyeonggi-do (KR)

(72) Inventors: Dong-Hyun Kim, Seoul (KR); Myung Joo Han, Seoul (KR)

(73) Assignees: University-Industry Cooperation Group of Kyung Hee University; Navipharm Co, Ltd

(*) Notice: Subject to any disclaimer, the term of this patent is extended or adjusted under 35 U.S.C. 154(b) by 0 days.

(21) Appl. No.: 16/760,689

(22) PCT Filed: Apr. 19, 2018

(86) PCT No.: PCT/KR2018/004590
§ 371 (c)(1),
(2) Date: Apr. 30, 2020

(87) PCT Pub. No.: WO2019/088379
PCT Pub. Date: May 9, 2019

(65) Prior Publication Data
US 2021/0260140 A1 Aug. 26, 2021

(30) Foreign Application Priority Data
Nov. 2, 2017 (KR) .......... 10-2017-0145420

(51) Int. Cl.
*A61K 35/747* (2015.01)
*A61K 35/745* (2015.01)
*A61K 35/00* (2006.01)
*C12R 1/25* (2006.01)

(52) U.S. Cl.
CPC .......... *A61K 35/745* (2013.01); *A61K 35/747* (2013.01); *C12R 2001/25* (2021.05)

(58) Field of Classification Search
None
See application file for complete search history.

(56) References Cited

U.S. PATENT DOCUMENTS

| | | | | |
|---|---|---|---|---|
| 11,202,811 B2* | 12/2021 | Kim | .......... | C12N 1/205 |
| 2016/0067289 A1 | 3/2016 | Berggren et al. | | |
| 2016/0074443 A1 | 3/2016 | Kim | | |
| 2019/0070229 A1* | 3/2019 | Choi | .......... | A61K 33/14 |

FOREIGN PATENT DOCUMENTS

| | | |
|---|---|---|
| CA | 2998841 | 3/2017 |
| JP | JR 9194384 | 7/1997 |
| KR | 1020150133284 A | 11/2015 |
| KR | 1020160007608 A | 1/2016 |
| KR | 1020160085235 | 7/2016 |
| KR | 20160098149 A | 8/2016 |
| KR | 101690738 B1 | 12/2016 |
| KR | 101709246 B1 | 2/2017 |
| KR | 1020170032848 | 3/2017 |
| KR | 1020170054682 | 5/2017 |
| KR | 101750468 B1 | 6/2017 |
| KR | 101784847 B1 | 10/2017 |
| WO | WO2014163568 A1 | 10/2014 |
| WO | WO2014184643 A1 | 11/2014 |
| WO | WO2015122717 A1 | 8/2015 |
| WO | WO2017037089 | 3/2017 |
| WO | WO2017196006 A1 | 11/2017 |

OTHER PUBLICATIONS

Kim et al. In: Proceedings of the Fall International Convention of the Pharmaceutical Society of Korea, Sponsored by The Korean Federation of Science and Technology Societies, p. 530, Abstract p. 5-13, Oct. 19-20, 2017.*
New Riverside University Dictionary (The Riverside Publishing Company, p. 933, 1984.*
International Search Report for Intl App No. PCT/KR2018/004590, dated Feb. 15, 2019 (6 pages).
KR Office Action for App No. KR 10-2018-0132834, dated Oct. 29, 2019 (7 pages).
Tabrizi et al., Prevalence of Gardnerella vaginalis and Atopobium vaginae in Virginal Women, Sexually Transmitted Diseases, 33(11):663-665 (Nov. 2006).
KR Decision to Grant for App No. KR 10-2018-0132834, dated Jul. 22, 2020 (with English Translation) (7 pages).
EP Extended Search Report in EP Appln. No. 19877635.3, dated Jan. 31, 2022, 6 pages.
Collins et al., "The potential of probiotics as a therapy for osteoporosis", Microbiology Spectrum, Aug. 2017, 5(4):1-16.
PCT International Preliminary Report on Patentability in International Appln. No. PCT/KR2018/004590, dated May 5, 2020, 16 pages with English Translation.
PCT International Preliminary Report on Patentability in International Appln. No. PCT/KR2019/005239, dated Apr. 27, 2021, 14 pages with English Translation.
PCT International Search Report and Written Opinion in International Appln. No. PCT/KR2019/005239, dated Aug. 16, 2019, 23 pages with English Translation.
Wallace et al., "The effects of probiotics on depressive symptoms in humans: A systematic review", Annals of General Psychiatry, 2017, 16(14):1-10.
Whitman et al., "Bacteria and the Fate of Estrogen in the Environment", Cell Chemical Biology, 2017, 24(6):652-653.
CA Office Action in Canadian Appln. No. 3081210, dated Apr. 8, 2022, 4 pages.
Kim et al., "Effects of *Lactobacillus plantarum* and *Bifidobacterium longum* on bacterial vaginosis and ovariectomized osteoporosis in mice," Thesis for the Degree of Master Pharmacy, Department of Life and Nanopharmaceutical Sciences, Graduate School of Kyung Hee University, Feb. 2019, pp. 1-42.

(Continued)

Primary Examiner — S. Devi
(74) Attorney, Agent, or Firm — Fish & Richardson P.C.

(57) ABSTRACT

The present invention relates to *Lactobacillus plantarum* NK3 and *Bifidobacterium longum* NK49, which are novel lactic acid bacteria and, more particularly, to a composition comprising novel lactic acid bacteria useful for prevention and treatment of inflammatory diseases.

10 Claims, 7 Drawing Sheets
Specification includes a Sequence Listing.

(56) References Cited

OTHER PUBLICATIONS

Kim et al., "*Lactobacillus plantarum* NK3 and *Bifidobacterium longum* NK49 ameliorated *Gardnerella vaginalis*-induced vaginosis in mice," 2017 Fall International Convention of The Pharmaceutical Society of Korea, Oct. 2017, 3 pages.
RU Office Action in Russian Appln. No. 2021112814, dated May 12, 2022, 22 pages (with English Translation).
Santoro et al., "Menopausal symptoms and their management," Endocrinology and Metabolism Clinics North Am., 2015, 44(3):497-515.

\* cited by examiner

LACTIC ACID BACTERIA AND USE THEREOF

TECHNICAL FIELD

The present invention relates to *Lactobacillus plantarum* and *Bifidobacterium longum*, which are novel lactic acid bacteria, and more particularly to a composition containing the novel lactic acid bacteria useful in preventing and treating inflammatory diseases.

BACKGROUND

Inflammation is a kind of defense reaction which occurs to biological tissues or organs against any external stimuli. In normal cases, the inflammatory reaction removes a material infected from the outside and regenerates a damaged tissue to restore a function thereof. However, if the inflammatory reaction is continuously caused by the secretion of inflammation-inducing cytokines, various inflammatory diseases occur depending on a site where the inflammatory reaction occurs.

On the other hand, vaginitis, which is one of female inflammatory diseases, is an intravaginal infectious disease caused by the growth of various anaerobic bacteria instead of bacteria normally present in the vagina. Recently, the incidence of vaginitis has increased due to women's greater use of feminine products and growing stress. Vaginitis is mostly bacterial vaginosis and fungal vaginitis. Bacterial vaginosis is typically caused by *Gardnerella vaginalis* or *Atopobium vaginae*, which is an anaerobic strain. Fungal vaginitis is mainly caused by *Candida albicans* (Sexually Transmitted Diseases, November 2006, vol 33, No. 11, 663-665).

Meanwhile, in case of bacterial vaginosis, symptoms may be ameliorated by using antibiotics. In case of fungal vaginitis, symptoms may be ameliorated by using an azole-based antifungal agent. However, these therapeutic agents may cause a phenomenon of another microbial substitution and thus have a problem in that it is difficult to expect a fundamental therapeutic effect. Thus, there is a need to develop a therapeutic agent capable of suppressing the inflammatory reaction so as to restore normal lactic acid bacteria while removing the vaginitis-causing bacteria from the vagina. However, research has not been sufficiently conducted.

Against these backdrops, while studying agents for preventing and treating inflammatory diseases, particularly vaginitis, the present inventors have identified that novel lactic acid bacteria isolated from kimchi and human feces may be valuably used in preventing and treating inflammatory diseases, particularly vaginitis not only by inhibiting inflammatory reactions, but also by showing a therapeutic effect on vaginitis while inhibiting the growth of vaginitis-causing bacteria, and thus have completed the present invention.

DETAILED DESCRIPTION OF THE INVENTION

Technical Problem

An objective of the present invention is to provide novel lactic acid bacteria of *Lactobacillus plantarum* and *Bifidobacterium longum*.

Another objective of the present invention is to provide a composition for preventing or treating inflammatory diseases, containing novel lactic acid bacteria.

Still another objective of the present invention is to provide a health functional food for preventing or ameliorating inflammatory diseases, containing novel lactic acid bacteria.

Technical Solution

In one aspect for achieving said objectives, the present invention provides *Lactobacillus plantarum* NK3 (depository institution: the Korean Culture Center of Microorganisms (KCCM), date of deposit: Aug. 4, 2017, and accession number: KCCM12089P).

The *Lactobacillus plantarum* NK3 of the present invention has a feature of being a novel lactic acid bacterium of *Lactobacillus plantarum*, which is isolated and identified from kimchi, which is a traditional fermented food.

A 16S rDNA sequence for identification and classification of *Lactobacillus plantarum* NK3 of the present invention is the same as SEQ ID NO: 1 attached to the present specification. Thus, *Lactobacillus plantarum* NK3 of the present invention may include the 16S rDNA of SEQ ID NO: 1.

As a result of analyzing said 16S rDNA sequence of SEQ ID NO: 1, this sequence was 99% homologous to that of generally known *Lactobacillus plantarum* strains, thus showing the highest molecular phylogenetic relationship with *Lactobacillus plantarum*. Thus, said lactic acid bacterium was identified as *Lactobacillus plantarum*, then named as *Lactobacillus plantarum* NK3, and then deposited to the KCCM on Aug. 4, 2017 (accession number: KCCM12089P).

The *Lactobacillus plantarum* NK3 of the present invention is a gram-positive bacterium and a cell form thereof is *bacillus*. More particularly, the physiological characteristics of *Lactobacillus plantarum* NK3 may be analyzed according to a conventional method in the art, and the results thereof are as shown in a following table 2. Particularly, *Lactobacillus plantarum* NK3 may use the following as a carbon source: L-arabinose, D-ribose, D-galactose, D-glucose, D-fructose, D-mannose, mannitol, sorbitol, α-methyl-D-mannoside, N-acetyl-glucosamine, amygdaline, arbutin, esculin, salicin, cellobiose, maltose, lactose, melibiose, sucrose, trehalose, melezitose, gentiobiose, D-turanose and gluconate.

In another aspect for achieving said objectives, the present invention provides *Bifidobacterium longum* NK49 (depository institution: the Korean Culture Center of Microorganisms (KCCM), date of deposit: Aug. 4, 2017, and accession number: KCCM12088P).

The *Bifidobacterium longum* NK49 of the present invention has a feature of being a novel lactic acid bacterium of *Bifidobacterium longum*, which is isolated and identified from human feces.

A 16S rDNA sequence for identification and classification of *Bifidobacterium longum* NK49 of the present invention is the same as SEQ ID NO: 2 attached to the present specification. Thus, *Bifidobacterium longum* NK49 of the present invention may include the 16S rDNA of SEQ ID NO: 2.

As a result of analyzing said 16S rDNA sequence of SEQ ID NO: 2, this sequence was 99% homologous to that of generally known *Bifidobacterium longum* strains, thus showing the highest molecular phylogenetic relationship with *Bifidobacterium longum*. Thus, said lactic acid bacterium was identified as *Bifidobacterium longum*, then named as *Bifidobacterium longum* NK49, and then deposited to the KCCM on Aug. 4, 2017 (accession number: KCCM12088P).

The *Bifidobacterium longum* NK49 of the present invention is a gram-positive bacterium and a cell form thereof is bacillus. More particularly, the physiological characteristics of *Bifidobacterium longum* NK49 may be analyzed according to a conventional method in the art, and the results thereof are as shown in a following table 3. Particularly, *Bifidobacterium longum* NK49 may use the following as a carbon source: L-arabinose, D-ribose, D-xylose, D-galactose, D-glucose, D-fructose, mannitol, sorbitol, α-methyl-D-glucoside, esculin, salicin, maltose, lactose, melibiose, sucrose, raffinose and D-turanose.

In still another aspect for achieving said objectives, the present invention provides a pharmaceutical composition for preventing or treating inflammatory diseases, containing *Lactobacillus plantarum* NK3 KCCM12089P, *Bifidobacterium longum* NK49 KCCM12088P or a mixture thereof.

The "*Lactobacillus plantarum* NK3" of the present invention is the same as described above.

Particularly, the *Lactobacillus plantarum* NK3 contained in the pharmaceutical composition of the present invention may be a live bacterial cell thereof, a dead bacterial cell thereof, a culture product thereof, a crushed product thereof or an extract thereof, but any type of *Lactobacillus plantarum* NK3 may be used without limitation, as long as it may achieve a preventive or therapeutic effect on inflammatory diseases.

The "*Bifidobacterium longum* NK49" of the present invention is the same as described above.

Particularly, the *Bifidobacterium longum* NK49 contained in the pharmaceutical composition of the present invention may be a live bacterial cell thereof, a dead bacterial cell thereof, a culture product thereof, a crushed product thereof or an extract thereof, but any type of *Lactobacillus plantarum* NK3 may be used without limitation, as long as it may achieve a preventive or therapeutic effect on inflammatory diseases.

In the present invention, the term "culture product" means an object obtained by culturing a lactic acid bacterium in a generally known liquid medium or solid medium, and is a concept encompassing a novel lactic acid bacterium in the present invention.

An inflammatory disease of the present invention may be at least one selected from the group including arthritis, gout, hepatitis, asthma, obesity, corneitis, gastritis, enteritis, nephritis, colitis, diabetes, tuberculosis, bronchitis, pleurisy, peritonitis, spondylitis, pancreatitis, inflammatory pain, urethritis, cystitis, vaginitis, arteriosclerosis, septicemia, burn, dermatitis, periodontitis and gingivitis.

In one embodiment of the present invention, it was identified that an inflammatory reaction is remarkably inhibited when macrophage isolated from a mouse is treated with *Lactobacillus plantarum* NK3 or *Bifidobacterium longum* NK49 along with lipopolysaccharide, which is an inflammatory reaction inducer (FIGS. 1 and 2). From the results, it was identified that the pharmaceutical composition containing said *Lactobacillus plantarum* NK3, *Bifidobacterium longum* NK49 or a mixture thereof may be valuably used in preventing and treating inflammatory diseases.

Particularly, said inflammatory disease may be vaginitis.

In one embodiment of the present invention, it was identified that *Lactobacillus plantarum* NK3, *Bifidobacterium longum* NK49 or a mixture thereof shows an effect of inhibiting the growth of *Gardnerella vaginalis* and *Atopobium vaginae*, which are vaginitis-inducing bacteria, and has an excellent effect of inhibiting infection with said *Gardnerella vaginalis* (FIGS. 3 to 5). Also, in one embodiment of the present invention, as a result of administering *Lactobacillus plantarum* NK3, *Bifidobacterium longum* NK49 or a mixture thereof into an animal model with induced vaginitis, it was identified that inflammations with edema caused by vaginitis bacteria and the number of vaginitis bacteria are decreased, an activity of myeloperoxidase, which is a representative inflammatory indicator in the vagina, is decreased, an expression of TNF-α is increased in the vaginal mucosa, and an expression of IL-10 is increased (FIGS. 6 to 10). From the results, it was identified that the pharmaceutical composition containing the *Lactobacillus plantarum* NK3, *Bifidobacterium longum* NK49 or a mixture thereof may be valuably used in preventing and treating vaginitis, which is a particular inflammatory disease.

Particularly, said inflammatory disease may be colitis.

In one embodiment of the present invention, as a result of administering *Lactobacillus plantarum* NK3, *Bifidobacterium longum* NK49 or a mixture thereof into an animal model with induced colitis, it was identified that a length of colon is recovered, an activity of myeloperoxidase is decreased, and the expression level and activity of cytokines, which are an inflammatory indicator, are inhibited (Table 6). From the results, it was identified that the pharmaceutical composition containing the *Lactobacillus plantarum* NK3, *Bifidobacterium longum* NK49 or a mixture thereof may be valuably used in preventing and treating colitis, which is a particular inflammatory disease.

The pharmaceutical composition according to the present invention may be prepared into a pharmaceutical dosage form by a well-known method in the art, so that an active component of the composition may be provided via a fast, suspended or prolonged release, after being administered into a mammal. When preparing a dosage form, the pharmaceutical composition according to the present invention may further contain a pharmaceutically acceptable carrier, to the extent that this carrier does not suppress an activity of a novel lactic acid bacterium.

Said pharmaceutically acceptable carrier may include conventionally used ones, for example, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propylhydroxybenzoate, talc, magnesium stearate, mineral oil and the like, but is not limited thereto. Also, the pharmaceutical composition of the present invention may contain a diluent or an excipient such as filler, extender, binder, humectant, disintegrant, surfactant, etc., or other pharmaceutically acceptable additives.

A dosage of the pharmaceutical composition according to the present invention needs to be a pharmaceutically effective amount. The "pharmaceutically effective amount" means an amount enough to prevent or treat inflammatory diseases at a reasonable benefit/risk ratio applicable to medical treatment. An effective dose level may be variously selected by those skilled in the art according to factors such as a formulation method, a patient's condition and weight, the patient's gender, age and degree of disease, a drug form, an administration route and period, an excretion rate, reaction sensitivity, etc. The effective amount may vary depending on a route of treatment, a use of excipients and a possibility of being used with other drugs, as recognized by those skilled in the art. However, in case of a preparation for oral administration to achieve a preferable effect, the composition of the present invention may be generally administered into an adult in an amount of 0.0001 to 100 mg/kg a day, preferably 0.001 to 100 mg/kg a day based on 1 kg of body weight. When the preparation is administered as above, *Lactobacillus plantarum* NK3, *Bifidobacterium longum* NK49 or a mixture thereof according to the present invention may be administered in an amount of $1 \times 10^2$ CFU/kg to $1 \times 10^{11}$ CFU/kg a day. This administration may be done once a day or several times a day by dividing the preparation. Said dosage does not limit the scope of the present invention in any aspect.

The pharmaceutical composition of the present invention may be administered to mammals such as mice, livestock, humans, etc. through various routes. Particularly, the pharmaceutical composition of the present invention may be orally or parenterally administered (for example, applied or injected intravenously, subcutaneously or intraperitoneally), but may be preferably orally administered. The pharmaceutical composition may be intravaginally administered to prevent and treat vaginitis. A solid preparation for oral administration may include powder, granule, tablet, capsule, soft capsule, pill, etc. A liquid preparation for oral administration may include a suspending agent, liquid for internal use, emulsion, syrup, aerosol, etc., but may also include various excipients, for example, humectant, sweetening agent, flavoring agent, preservative, etc. in addition to water and liquid paraffin, which are frequently used simple diluents. A preparation for parenteral administration may be used by being formulated into a dosage form of external preparation and sterilized injectable preparation such as sterilized aqueous solution, liquid, non-aqueous solvent, suspending agent, emulsion, eye drop, eye ointment, syrup, suppository, aerosol, etc., according to respective conventional methods, and preferably may be used by preparing a pharmaceutical composition of cream, gel, patch, spray, ointment, plaster, lotion, liniment, eye ointment, eye drop, paste or cataplasma, but is not limited thereto. A preparation for local administration may be an anhydrous or aqueous form depending on a clinical prescription. As the non-aqueous solvent and the suspending agent above, propylene glycol, polyethylene glycol, vegetable oil like olive oil, injectable ester like ethyl oleate, etc. may be used. As a base of the suppository, the following may be used: Witepsol, Macrogol, TWEEN 61, cacao butter, laurinum, glycerogelatin, etc.

In still another aspect for achieving said objectives, the present invention provides a method for preventing or treating inflammatory diseases, including administering *Lactobacillus plantarum* NK3, *Bifidobacterium longum* NK49 or a mixture thereof into a subject.

In the present invention, the terms "*Lactobacillus plantarum* NK3," "*Bifidobacterium longum* NK49," "administration," "inflammatory disease" and the like are the same as described above.

Said subject refers to an animal, and may be typically a mammal, on which treatment using the novel lactic acid bacteria of the present invention may show a beneficial effect. A preferable example of this subject may include primates like humans. Also, these subjects may include all the subjects having a symptom of inflammatory diseases, or having a risk of having the symptom.

In still another aspect, the present invention provides a health functional food for preventing or ameliorating inflammatory diseases, containing *Lactobacillus plantarum* NK3 KCCM12089P, *Bifidobacterium longum* NK49 KCCM12088P or a mixture thereof.

In the present invention, the terms "*Lactobacillus plantarum* NK3," "*Bifidobacterium longum* NK49," "administration," "inflammatory disease" and the like are the same as described above.

The health functional food, which puts an emphasis on a body modulating function of food, is a food, which is given value added to work and express for a particular purpose by using a physical, biochemical or bioengineering method. A component of this health functional food is designed and processed to fully exert a body modulating function in vivo, which is involved in defending a living body, adjusting a body rhythm, preventing a disease and recovering from the disease, and may contain food supplementary additives, sweeteners or functional raw materials, which are acceptable as food.

In case of using *Lactobacillus plantarum* NK3 or *Bifidobacterium longum* NK49 of the present invention as a health functional food (or health functional beverage additives), said novel lactic acid bacteria may be added thereto as they are, used along with other food or food ingredients, or appropriately used according to a conventional method. A mixed amount of said *Lactobacillus plantarum* NK3 or *Bifidobacterium longum* NK49 may be appropriately determined depending on a purpose of use thereof (prevention, health, improvement or therapeutic treatment).

Said health functional food may contain various nutrients, vitamins, minerals (electrolytes), flavoring agents such as synthetic flavoring agents, natural flavoring agents and the like, coloring agents and enhancers (cheese, chocolate, etc.), pectic acid and salts thereof, organic acid, protective colloidal thickeners, pH adjusting agents, stabilizers, preservatives, glycerin, alcohol, carbonators used in carbonated beverages, etc. Also, the health functional food of the present invention may contain pulp for preparing fruit and vegetable based beverages. These components may be used alone or in combination, and a ratio of the additives is generally selected from a range of 0.001 to 50 parts by weight with regard to the total weight of the composition.

A type of said health functional food has no particular limitation. Food, to which said *Lactobacillus plantarum* NK3 or *Bifidobacterium longum* NK49 may be added, includes sausage, meats, bread, chocolates, snacks, candies, confectionery, ramen, pizza, other noodles, chewing gums, dairy products including ice creams, various soups, beverages, teas, health drinks, alcohol beverages, vitamin complexes and the like. In case of being formulated into beverages, a liquid component, which is added to the beverages in addition to the novel lactic acid bacteria, may include various flavors, natural carbohydrates or the like as an additional component just as contained in conventional beverages, but is not limited thereto. The natural carbohydrates mentioned above may be monosaccharide (ex. glucose, fructose, etc.), disaccharide (ex. maltose, sucrose, etc.) and polysaccharide (ex. conventional sugar such as dextrin, cyclodextrin, etc.), as well as sugar alcohol such as xylitol, sorbitol, erythritol, etc.

In still another aspect, the present invention provides a use of *Lactobacillus plantarum* NK3 KCCM12089P, *Bifidobacterium longum* NK49 KCCM12088P or a mixture thereof for preparing a drug for treating inflammatory diseases.

In still another aspect, the present invention provides a composition containing *Lactobacillus plantarum* NK3 KCCM12089P, *Bifidobacterium longum* NK49 KCCM12088P or a mixture thereof for a use in treating inflammatory diseases.

In still another aspect, the present invention provides a use of *Lactobacillus plantarum* NK3 KCCM12089P, *Bifidobacterium longum NK49 KCCM12088P or a mixture thereof for treating inflammatory diseases.

The numerical values described in the present specification as above should be interpreted to include a range of equivalents thereof, unless otherwise stated.

Hereinafter, the present invention will be described in detail through preferred Examples for better understanding of the present invention. However, the following Examples are provided only for the purpose of illustrating the present invention, and thus the present invention is not limited thereto.

Advantageous Effects

*Lactobacillus plantarum* NK3, *Bifidobacterium longum* NK49 or a mixture thereof, which is a novel lactic acid bacterium according to the present invention, has an effect of inhibiting inflammatory reactions. Thus, the novel lactic acid bacteria according to the present invention may be used as a composition for preventing or treating inflammatory diseases, and particularly effective in treating and preventing colitis and vaginitis.

G: Group treated with *Gardnerella vaginalis* only; GL5, GL6, GL7: Group treated with *Gardnerella vaginalis* and then treated with *Lactobacillus plantarum* at $1\times10^6$ CFU/mL, $1\times10^7$ CFU/mL and $1\times10^8$ CFU/mL respectively; and GB5, GB6, GB7: Group treated with *Gardnerella vaginalis* and then treated with *Bifidobacterium longum* at $1\times10^6$ CFU/mL, $1\times10^7$ CFU/mL and $1\times10^8$ CFU/mL respectively.

Figure 6:
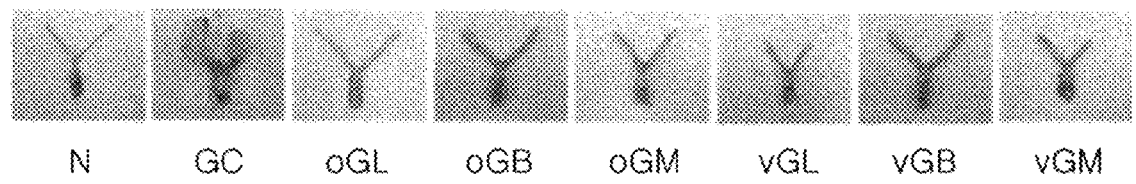

FIG. 6 is a view showing an identified effect of *Lactobacillus plantarum* NK3, *Bifidobacterium longum* NK49 and a mixture thereof, which are novel lactic acid bacteria, on inhibiting inflammations in the vagina and the uterus.

N: Normal group; GC: Group infected with *Gardnerella vaginalis* only; oGL, oGB, oGM: Group of experimental animals infected with *Gardnerella vaginalis*, orally dosed with respective *Lactobacillus plantarum*, *Bifidobacterium longum* or a mixture thereof; and vGL, vGB, vGM: Group of experimental animals infected with *Gardnerella vaginalis*, intravaginally dosed with respective *Lactobacillus plantarum*, *Bifidobacterium longum* or a mixture thereof. Hereinafter the same.

Figure 7:
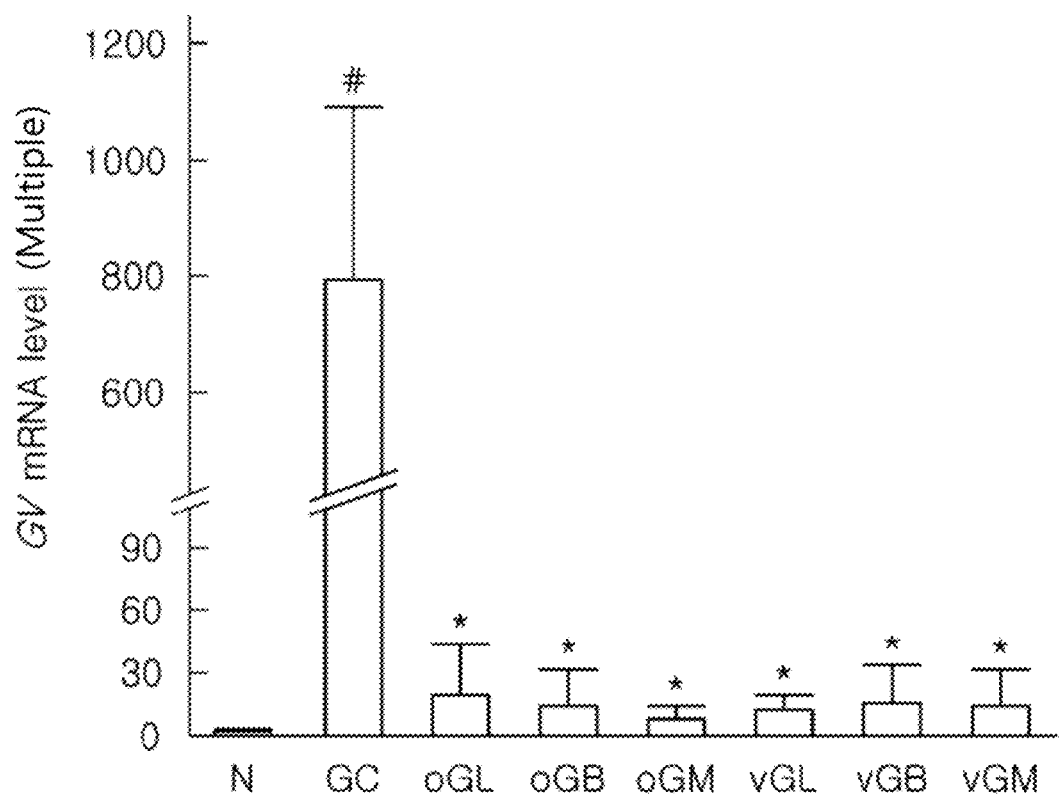

FIG. 7 is a graph showing an inhibitory capacity of *Lactobacillus plantarum* NK3, *Bifidobacterium longum* NK49 and a mixture thereof, which are novel lactic acid bacteria, against infection with *Gardnerella vaginalis*.

Figure 8:
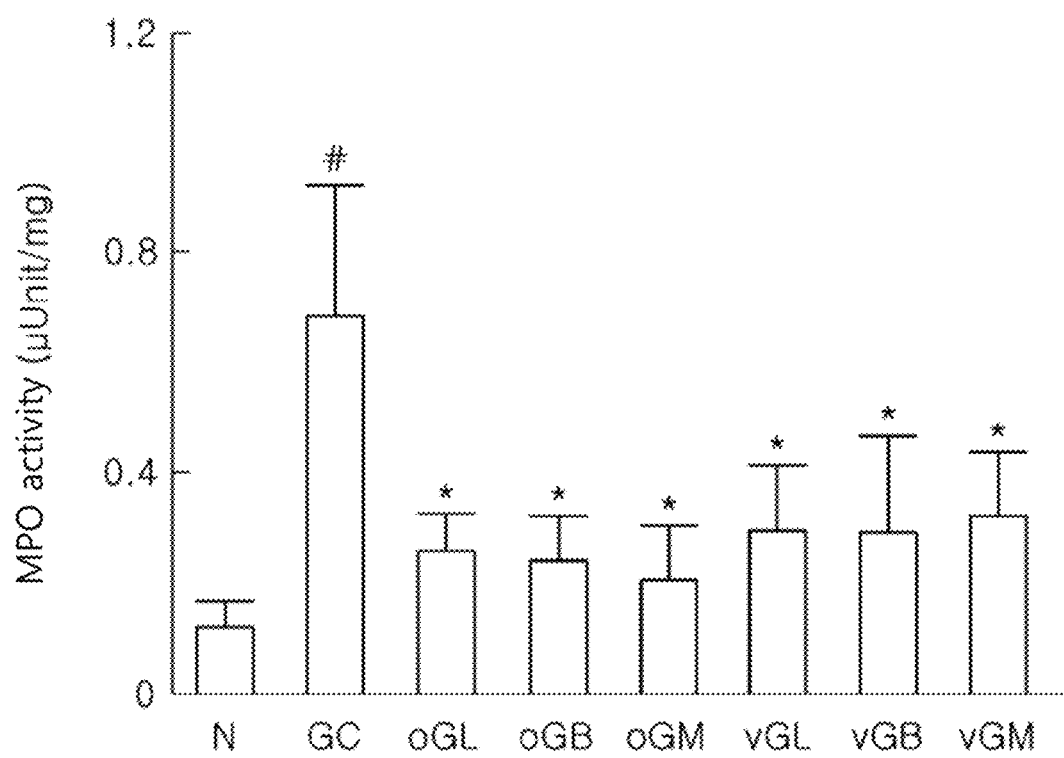

FIG. 8 is a graph showing an inhibitory capacity of *Lactobacillus plantarum* NK3, *Bifidobacterium longum* NK49 and a mixture thereof, which are novel lactic acid bacteria, against an activity of myeloperoxidase.

Figure 9:
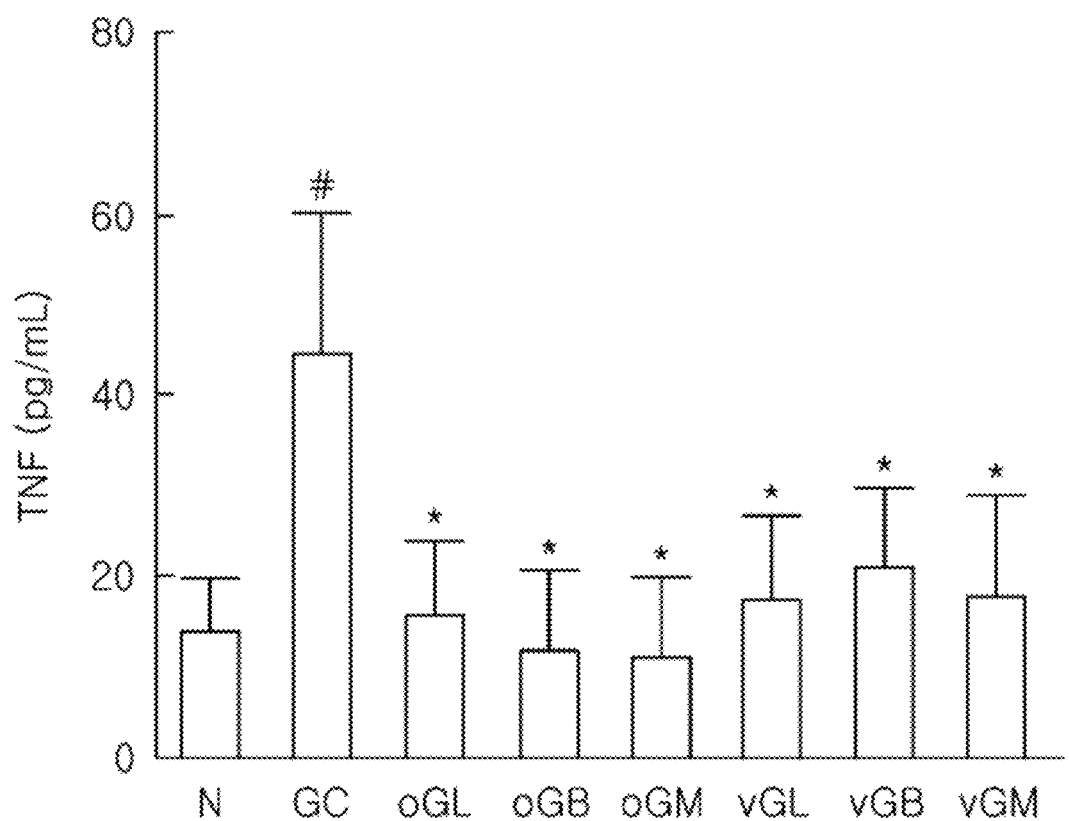

FIG. 9 is a graph showing an inhibitory capacity of *Lactobacillus plantarum* NK3, *Bifidobacterium longum* NK49 and a mixture thereof, which are novel lactic acid bacteria, against an expression of TNF-α.

Figure 10:
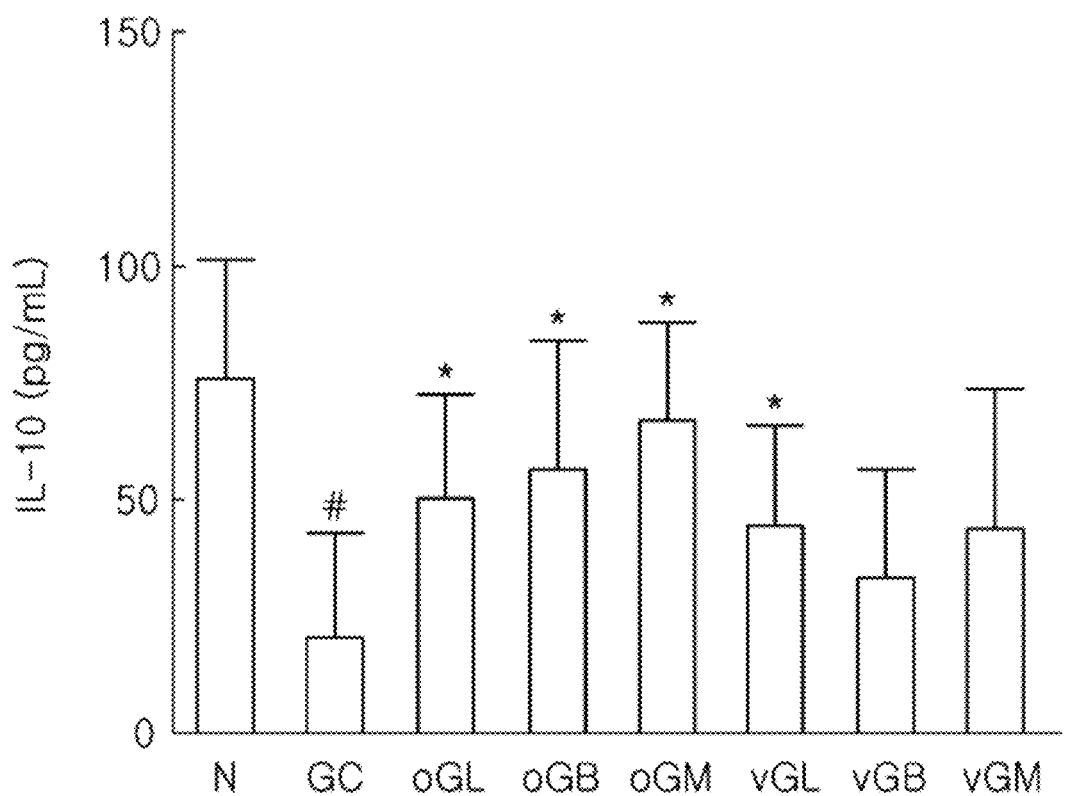

FIG. 10 is a graph showing an increasing capacity of *Lactobacillus plantarum* NK3, *Bifidobacterium longum* NK49 and a mixture thereof, which are novel lactic acid bacteria, for an expression of IL-10.

Figure 11:
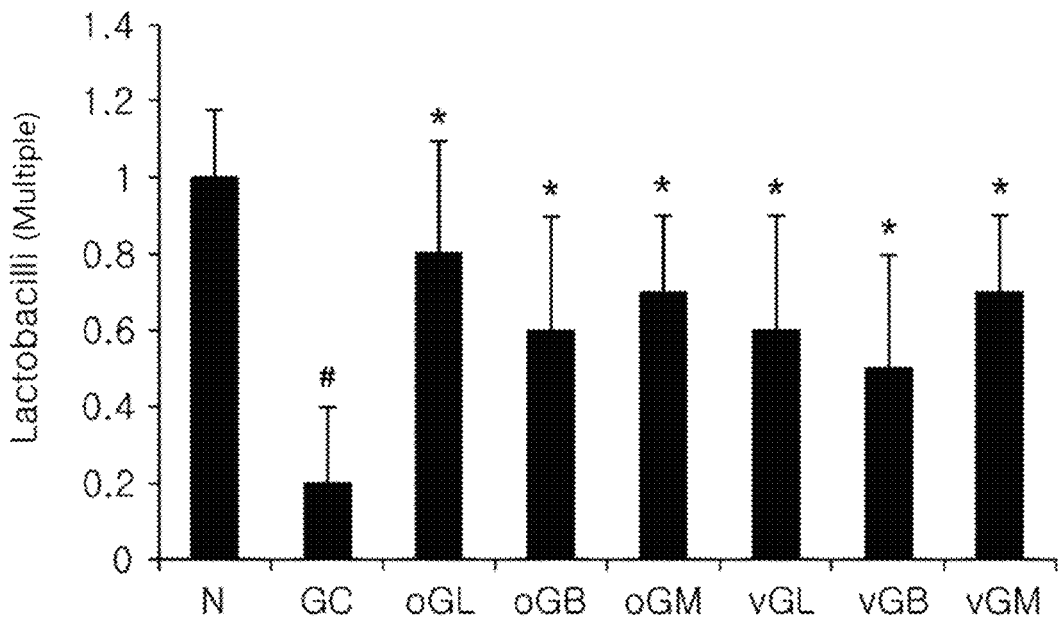

FIG. 11 is a graph showing an effect of *Lactobacillus plantarum* NK3, *Bifidobacterium longum* NK49 and a mixture thereof, which are novel lactic acid bacteria, on recovering Lactobacilli in the vagina.

MODE FOR INVENTION

Hereinafter, the present invention will be described in detail through preferred Examples for better understanding of the present invention. However, the following Examples are provided only for the purpose of illustrating the present invention, and thus the present invention is not limited thereto.

Example 1: Isolation and Identification of Lactic Acid Bacteria (1) Isolation of lactic acid bacteria from human feces Human feces were inserted and suspended in GAM liquid medium (GAM broth; Nissui Pharmaceutical, Japan). After that, the supernatant was taken and transplanted into BL agar medium (Nissui Pharmaceutical, Japan), and then anaerobically cultured at 37° C. for about 48 hours, so as to isolate colony-forming strains therefrom.

(2) Isolation of Lactic Acid Bacteria from Kimchi

Cabbage kimchi, radish kimchi or green onion kimchi was crushed respectively, after which crushed supernatant was taken and transplanted into MRS agar medium (Difco, USA), and then anaerobically cultured at 37° C. for about 48 hours, so as to isolate colony-forming strains therefrom.

(3) Identification of Isolated Lactic Acid Bacteria

Physiological characteristics and 16S rDNA sequences of the strains isolated from human feces or kimchi were analyzed to identify species of the strains, and then names were given to the strains. Strain names given to lactic acid bacteria are the same as shown in the following table 1. Particularly, the lactic acid bacteria isolated from kimchi were five species of *Lactobacillus plantarum* (management nos. 1 to 5 of Table 1), five species of *Lactobacillus brevis* (management nos. 6 to 10 of Table 1), five species of *Lactobacillus sakei* (management nos. 11 to 15 of Table 1), and five species of *Lactobacillus curvatus* (management nos. 16 to 20 of Table 1). The lactic acid bacteria isolated from human feces were five species of *Lactobacillus rhamnosus* (management nos. 21 to 25 of Table 1), five species of *Lactobacillus plantarum* (management nos. 26 to 30 of Table 1), five species of *Lactobacillus reuteri* (management nos. 31 to 35 of Table 1), four species of *Lactobacillus johnsonii* (management nos. 36 to 39 of Table 1), three species of *Lactobacillus* mucosae (management nos. 40 to 42 of Table 1), three species of *Bifidobacterium adolescentis*

(management nos. 43 to 45 of Table 1), and five species of *Bifidobacterium longum* (management nos. 46 to 50 of Table 1).

TABLE 1

| Management no. | Strain name |
|---|---|
| 1 | Lactobacillus plantarum NK1 |
| 2 | Lactobacillus plantarum NK2 |
| 3 | Lactobacillus plantarum NK3 |
| 4 | Lactobacillus plantarum NK4 |
| 5 | Lactobacillus plantarum NK5 |
| 6 | Lactobacillus brevis NK6 |
| 7 | Lactobacillus brevis NK7 |
| 8 | Lactobacillus brevis NK8 |
| 9 | Lactobacillus brevis NK9 |
| 10 | Lactobacillus brevis NK10 |
| 11 | Lactobacillus sakei NK11 |
| 12 | Lactobacillus sakei NK12 |
| 13 | Lactobacillus sakei NK13 |
| 14 | Lactobacillus sakei NK14 |
| 15 | Lactobacillus sakei NK15 |
| 16 | Lactobacillus curvatus NK16 |
| 17 | Lactobacillus curvatus NK17 |
| 18 | Lactobacillus curvatus NK18 |
| 19 | Lactobacillus curvatus NK19 |
| 20 | Lactobacillus curvatus NK20 |
| 21 | Lactobacillus rhamnosus NK21 |
| 22 | Lactobacillus rhamnosus NK22 |
| 23 | Lactobacillus rhamnosus NK23 |
| 24 | Lactobacillus rhamnosus NK24 |
| 25 | Lactobacillus rhamnosus NK25 |
| 26 | Lactobacillus plantarum NK26 |
| 27 | Lactobacillus plantarum NK27 |
| 28 | Lactobacillus plantarum NK28 |
| 29 | Lactobacillus plantarum NK29 |
| 30 | Lactobacillus plantarum NK30 |
| 31 | Lactobacillus reuteri NK31 |
| 32 | Lactobacillus reuteri NK32 |
| 33 | Lactobacillus reuteri NK33 |
| 34 | Lactobacillus reuteri NK34 |
| 35 | Lactobacillus reuteri NK35 |
| 36 | Lactobacillus johnsonii NK36 |
| 37 | Lactobacillus johnsonii NK37 |
| 38 | Lactobacillus johnsonii NK38 |
| 39 | Lactobacillus johnsonii NK39 |
| 40 | Lactobacillus mucosae NK40 |
| 41 | Lactobacillus mucosae NK41 |
| 42 | Lactobacillus mucosae NK42 |
| 43 | Bifidobacterium adolescentis NK43 |
| 44 | Bifidobacterium adolescentis NK44 |
| 45 | Bifidobacterium adolescentis NK45 |
| 46 | Bifidobacterium longum NK46 |
| 47 | Bifidobacterium longum NK47 |
| 48 | Bifidobacterium longum NK48 |
| 49 | Bifidobacterium longum NK49 |
| 50 | Bifidobacterium longum NK50 |

(4) Physiological Characteristics of Novel Lactic Acid Bacterium *Lactobacillus plantarum* NK3

Out of strains described in Table 1 above, it was identified that *Lactobacillus plantarum* NK3 (accession number KCCM12089P) is a gram-positive *bacillus*. Also, it was shown that 16S rDNA of *Lactobacillus plantarum* NK3 has a sequence of SEQ ID NO: 1. As a result of comparing the 16S rDNA sequence of *Lactobacillus plantarum* NK3 through BLAST search, it was shown that a *Lactobacillus plantarum* strain having the same 16S rDNA sequence is not searched at all, and the sequence was 99% homologous to the 16S rDNA sequence of a generally known *Lactobacillus plantarum* strain.

Out of physiological characteristics of *Lactobacillus plantarum* NK3, availability of carbon source was analyzed with a sugar fermentation test using API 50 CHL kit. The results thereof are the same as shown in a following table 2.

In Table 2 below, "+" indicates that the availability of carbon source is positive and "−" indicates that the availability of carbon source is negative.

TABLE 2

| Carbon source | NK3 | Carbon source | NK3 |
|---|---|---|---|
| CONTROL | − | Esculin | + |
| Glycerol | − | Salicin | + |
| Erythritol | − | Cellobiose | + |
| D-arabinose | − | Maltose | + |
| L-arabinose | + | Lactose | + |
| D-ribose | + | Melibiose | + |
| D-xylose | − | Sucrose | + |
| L-xylose | − | Trehalose | + |
| D-adonitol | − | Inulin | − |
| Methyl-BD-xylopyranoside | − | Melezitose | + |
| D-galactose | + | Raffinose | − |
| D-glucose | + | Starch | − |
| D-fructose | + | Glycogen | − |
| D-mannose | + | Xylitol | − |
| L-sorbose | − | Gentiobiose | + |
| Rhamnosus | − | D-furanose | + |
| Dulcitol | − | D-lyxose | − |
| Inositol | − | D-tagatose | − |
| Mannitol | + | D-fucose | − |
| Solbitol | + | L-fucose | − |
| α-methyl-D-mannoside | ± | D-arabitol | − |
| α-methyl-D-glucoside | − | L-arabitol | − |
| N-acetyl-glucosamine | + | Gluconate | ± |
| Amygdalin | + | 2-keto-gluconate | − |
| Arbutin | + | 5-keto-gluconate | − |

(5) Physiological Characteristics of Novel Lactic Acid Bacterium *Bifidobacterium longum* NK49

Out of strains described in Table 1 above, it was identified that *Bifidobacterium longum* NK49 (accession number KCCM12088P) is a gram-positive *bacillus*. Also, it was shown that 16S rDNA of *Bifidobacterium longum* NK49 has a sequence of SEQ ID NO: 2. As a result of comparing the 16S rDNA sequence of *Bifidobacterium longum* NK49 through BLAST search, it was shown that a *Bifidobacterium longum* strain having the same 16S rDNA sequence is not searched at all, and 99% homologous to the 16S rDNA sequence of a generally known *Bifidobacterium longum* strain.

Out of physiological characteristics of *Bifidobacterium longum* NK49, availability of carbon source was analyzed with a sugar fermentation test using API 50 CHL kit. The results thereof are the same as shown in a following table 3. In Table 3 below, "+" indicates that the availability of carbon source is positive and "−" indicates that the availability of carbon source is negative.

TABLE 3

| Carbon source | NK49 | Carbon source | NK49 |
|---|---|---|---|
| CONTROL | − | Esculin | + |
| Glycerol | − | Salicin | + |
| Erythritol | − | Cellobiose | − |
| D-arabinose | − | Maltose | + |
| L-arabinose | + | Lactose | + |
| D-ribose | + | Melibiose | + |
| D-xylose | ± | Sucrose | + |
| L-xylose | − | Trehalose | − |
| D-adonitol | − | Inulin | − |
| Methyl-BD-xylopyranoside | − | Melezitose | − |
| D-galactose | + | Raffinose | + |
| D-glucose | + | Starch | − |
| D-fructose | + | Glycogen | − |
| D-mannose | − | Xylitol | − |
| L-sorbose | − | Gentiobiose | − |
| Rhamnosus | − | D-turanose | ± |

TABLE 3-continued

| Carbon source | NK49 | Carbon source | NK49 |
|---|---|---|---|
| Dulcitol | − | D-lyxose | − |
| Inositol | − | D-tagatose | − |
| Mannitol | + | D-fucose | − |
| Sorbitol | + | L-fucose | − |
| α-methyl-D-mannoside | − | D-arabitol | − |
| α-methyl-D-glucoside | ± | L-arabitol | − |
| N-acetyl-glucosamine | − | Gluconate | − |
| Amygdalin | − | 2-keto-gluconate | − |
| Arbutin | − | 5-keto-gluconate | − |

Example 2: Comparison of Activity of Isolated Lactic Acid Bacteria (1) Antioxidant Activity (In Vitro)

DPPH (2,2-Diphenyl-1-picrylhydrazyl) was dissolved in ethanol to reach a 0.2 mM concentration, such that a DPPH solution was prepared. A suspension of lactic acid bacteria ($1 \times 10^6$ CFU/m2) or a vitamin C solution (1 g/m2) was inserted into 0.1 ml of said DPPH solution, and then cultured at 37° C. for 20 minutes. A culture fluid was centrifuged at 3000 rpm for five minutes, such that supernatant was obtained. After that, an absorbance of the supernatant was measured at 517 nm, and then antioxidant activity of isolated lactic acid bacteria was calculated accordingly. Antioxidant activity for each lactic acid bacterium is the same as shown in a following table 4.

(2) Measurement of Inflammatory Indicators in Macrophage 2 ml of sterilized 4% Thioglycolate was intraperitoneally administered into a C57BL/6 mouse (male, 6 weeks old and 20-23 g). In 96 hours later, the mouse was anesthetized, and then 8 ml of RPMI 1640 medium was intraperitoneally administered to the mouse. In 5 to 10 minutes later, the RPMI medium (macrophage) was intraperitoneally extracted from the mouse, then centrifuged at 1000 g for 10 minutes, and then washed twice again with RPMI 1640 medium. Said macrophage was plated in a 24-well plate at $0.5 \times 10^6$ per well, and then treated with the isolated lactic acid bacteria (final treatment concentration: $1 \times 10^4$ cfu/ml, hereinafter the same) and lipopolysaccharide (LPS), which is an inflammatory reaction inducer, for 2 or 24 hours, such that supernatant and cells were obtained therefrom. The obtained cells were inserted into an RIPA buffer (Gibco) and homogenized. An expression level of cytokines such as TNF-α, IL-10, etc. was measured from a culture supernatant treated for 24 hours and expression levels of p65 (NF-κB), p-p65 (phosphor-NF-κB) and β-actin were measured from the cells obtained with treatment for two hours through an immunoblotting method. Expression levels of inflammation indicators for each lactic acid bacterium are the same as shown in a following table 4.

(Criteria when measuring activity in Table 4: +++, >90%, very strong; ++, >60-90%, strong; +, >20-60%, weak; and −, <20%, insignificant effect, the same as Table 5)

TABLE 4

| Management no. | Strain name | Antioxidant activity | TNF-α inhibitory capacity | IL-10 expression increase | NF-kB inhibitory capacity |
|---|---|---|---|---|---|
| 1 | Lactobacillus plantarum NK1 | + | + | + | + |
| 2 | Lactobacillus plantarum NK2 | + | ++ | + | + |
| 3 | Lactobacillus plantarum NK3 | +++ | +++ | +++ | +++ |
| 4 | Lactobacillus plantarum NK4 | + | + | + | ++ |
| 5 | Lactobacillus plantarum NK5 | ++ | ++ | ++ | ++ |
| 6 | Lactobacillus brevis NK6 | + | + | + | + |
| 7 | Lactobacillus brevis NK7 | + | + | + | + |
| 8 | Lactobacillus brevis NK8 | + | + | + | + |
| 9 | Lactobacillus brevis NK9 | + | + | + | + |
| 10 | Lactobacillus brevis NK10 | − | + | + | + |
| 11 | Lactobacillus sakei NK11 | + | + | + | + |
| 12 | Lactobacillus sakei NK12 | − | ++ | + | + |
| 13 | Lactobacillus sakei NK13 | − | ++ | ++ | + |
| 14 | Lactobacillus sakei NK14 | − | + | + | + |
| 15 | Lactobacillus sakei NK15 | + | + | + | + |
| 16 | Lactobacillus curvatus NK16 | + | + | + | + |
| 17 | Lactobacillus curvatus NK17 | + | + | + | + |
| 18 | Lactobacillus curvatus NK18 | + | + | + | + |
| 19 | Lactobacillus curvatus NK19 | + | + | + | + |
| 20 | Lactobacillus curvatus NK20 | + | + | + | + |
| 21 | Lactobacillus rhamnosus NK21 | + | + | + | + |
| 22 | Lactobacillus rhamnosus NK22 | + | + | + | + |
| 23 | Lactobacillus rhamnosus NK23 | + | + | + | + |
| 24 | Lactobacillus rhamnosus NK24 | ++ | + | + | + |
| 25 | Lactobacillus rhamnosus NK25 | ++ | ++ | ++ | ++ |
| 26 | Lactobacillus plantarum NK26 | + | + | + | + |
| 27 | Lactobacillus plantarum NK27 | + | + | + | + |
| 28 | Lactobacillus plantarum NK28 | + | + | + | + |
| 29 | Lactobacillus plantarum NK29 | + | + | + | + |
| 30 | Lactobacillus plantarum NK30 | + | + | + | + |
| 31 | Lactobacillus reuteri NK31 | + | + | + | + |
| 32 | Lactobacillus reuteri NK32 | ++ | ++ | ++ | ++ |
| 33 | Lactobacillus reuteri NK33 | +++ | ++ | ++ | ++ |
| 34 | Lactobacillus reuteri NK34 | + | + | + | + |
| 35 | Lactobacillus reuteri NK35 | + | + | + | + |
| 36 | Lactobacillus johnsonii NK36 | ++ | ++ | ++ | + |
| 37 | Lactobacillus johnsonii NK37 | ++ | ++ | ++ | ++ |
| 38 | Lactobacillus johnsonii NK38 | + | + | + | + |
| 39 | Lactobacillus johnsonii NK39 | + | + | + | + |

TABLE 4-continued

| Management no. | Strain name | Antioxidant activity | TNF-α inhibitory capacity | IL-10 expression increase | NF-kB inhibitory capacity |
|---|---|---|---|---|---|
| 40 | Lactobacillus mucosae NK40 | ++ | ++ | ++ | ++ |
| 41 | Lactobacillus mucosae NK41 | ++ | ++ | +++ | +++ |
| 42 | Lactobacillus mucosae NK42 | + | + | + | + |
| 43 | Bifidobacterium adolescentis NK43 | + | + | + | + |
| 44 | Bifidobacterium adolescentis NK44 | ++ | ++ | ++ | ++ |
| 45 | Bifidobacterium adolescentis NK45 | + | + | + | + |
| 46 | Bifidobacterium longum NK46 | +++ | ++ | +++ | +++ |
| 47 | Bifidobacterium longum NK47 | ++ | ++ | ++ | ++ |
| 48 | Bifidobacterium longum NK48 | + | + | + | + |
| 49 | Bifidobacterium longum NK49 | +++ | +++ | +++ | +++ |
| 50 | Bifidobacterium longum NK50 | + | + | + | + |

(3) Effect on ZO-1 Protein Expression in Caco2 Cells

Caco2 cells, which are colon cancer cells, were purchased from the Korean Cell Line Bank, then cultured in RPMI 1640 medium for 48 hours, and then were seeded in a 12-well plate at $2 \times 10^6$ cells per well. Each well was treated with 1 μg of LPS only, or treated with 1 μg of LPS and $1 \times 10^4$ CFU of lactic acid bacteria together, and then cultured for 24 hours. After that, the cultured cells were collected from each well, and an expression level of ZO-1, which is a tight junction protein, was measured by an immunoblotting method. Expression levels of ZO-1 for each lactic acid bacterium are the same as shown in a following table 5.

TABLE 5

| Management no. | Strain name | ZO-1 Expression increase |
|---|---|---|
| 1 | Lactobacillus plantarum NK1 | + |
| 2 | Lactobacillus plantarum NK2 | + |
| 3 | Lactobacillus plantarum NK3 | ++ |
| 4 | Lactobacillus plantarum NK4 | + |
| 5 | Lactobacillus plantarum NK5 | ++ |
| 6 | Lactobacillus brevis NK6 | + |
| 7 | Lactobacillus brevis NK7 | + |
| 8 | Lactobacillus brevis NK8 | + |
| 9 | Lactobacillus brevis NK9 | + |
| 10 | Lactobacillus brevis NK10 | − |
| 11 | Lactobacillus sakei NK11 | + |
| 12 | Lactobacillus sakei NK12 | − |
| 13 | Lactobacillus sakei NK13 | + |
| 14 | Lactobacillus sakei NK14 | + |
| 15 | Lactobacillus sakei NK15 | + |
| 16 | Lactobacillus curvatus NK16 | + |
| 17 | Lactobacillus curvatus NK17 | + |
| 18 | Lactobacillus curvatus NK18 | + |
| 19 | Lactobacillus curvatus NK19 | + |
| 20 | Lactobacillus curvatus NK20 | + |
| 21 | Lactobacillus rhamnosus NK21 | + |
| 22 | Lactobacillus rhamnosus NK22 | + |
| 23 | Lactobacillus rhamnosus NK23 | + |
| 24 | Lactobacillus rhamnosus NK24 | ++ |
| 25 | Lactobacillus rhamnosus NK25 | + |
| 26 | Lactobacillus plantarum NK26 | + |
| 27 | Lactobacillus plantarum NK27 | + |
| 28 | Lactobacillus plantarum NK28 | + |
| 29 | Lactobacillus plantarum NK29 | + |
| 30 | Lactobacillus plantarum NK30 | + |
| 31 | Lactobacillus reuteri NK31 | + |
| 32 | Lactobacillus reuteri NK32 | ++ |
| 33 | Lactobacillus reuteri NK33 | ++ |
| 34 | Lactobacillus reuteri NK34 | + |
| 35 | Lactobacillus reuteri NK35 | + |
| 36 | Lactobacillus johnsonii NK36 | + |
| 37 | Lactobacillus johnsonii NK37 | ++ |
| 38 | Lactobacillus johnsonii NK38 | + |
| 39 | Lactobacillus johnsonii NK39 | + |
| 40 | Lactobacillus mucosae NK40 | ++ |
| 41 | Lactobacillus mucosae NK41 | ++ |
| 42 | Lactobacillus mucosae NK42 | + |
| 43 | Bifidobacterium adolescentis NK43 | + |
| 44 | Bifidobacterium adolescentis NK44 | ++ |
| 45 | Bifidobacterium adolescentis NK45 | + |
| 46 | Bifidobacterium longum NK46 | ++ |
| 47 | Bifidobacterium longum NK47 | + |
| 48 | Bifidobacterium longum NK48 | + |
| 49 | Bifidobacterium longum NK49 | + |
| 50 | Bifidobacterium longum NK50 | + |

(5) Experimental Results

As a result of evaluating an activity of isolated lactic acid bacteria, it was identified that *Lactobacillus plantarum* NK3 and *Bifidobacterium longum* NK49, which are novel lactic bacteria out of the isolated lactic acid bacteria, increase an expression level of ZO-1, which is a tight junction protein, thereby showing an excellent antioxidant activity and an excellent effect of inhibiting inflammatory reactions (Tables 4 and 5).

Example 3: Measurement of Inhibitory Capacity Against Inflammatory Reactions of Macrophage In Example 2 above, it was identified that there is an effect of inhibiting inflammatory reactions depending on a concentration of administration of *Lactobacillus plantarum* NK3 and *Bifidobacterium longum* NK49, which are novel lactic acid bacteria having excellent antioxidant activity and an excellent effect of inhibiting inflammatory reactions.

Particularly, 2 ml of sterilized 4% Thioglycolate was intraperitoneally administered into a C57BL/6 mouse (male, 20-23 g). In 96 hours later, the mouse was anesthetized, and then 8 ml of RPMI 1640 medium was intraperitoneally administered into the mouse. In 5 to 10 minutes later, the RPMI medium (macrophage) was intraperitoneally extracted from the mouse, then centrifuged at 1000 g for 10 minutes, and then washed twice again with RPMI 1640 medium. After being cultured in a 24-well plate for five hours, attached cells were used as macrophage. The macrophage was plated at $0.5 \times 10^6$ per well, and treated with $10^3$, $10^4$ and $10^5$ CFU/mL of *Lactobacillus plantarum* NK3 and *Bifidobacterium longum* NK49, which are novel lactic acid bacteria, as well as lipopolysaccharide (LPS), which is an inflammatory reaction inducer, for 90 minutes or 24 hours, such that supernatant and cells were obtained therefrom. The obtained cells were inserted into an RIPA buffer (Gibco) and homogenized. Expression levels of p65 (NF-κB), p-p65 (phosphor-NF-kB) and β-actin were measured from the cells obtained with treatment for 90 minutes through an immunoblotting method. An expression level of TNF-α cytokines was measured by ELISA kit (Ebioscience, San Diego, Calif., USA) from the culture supernatant obtained after treatment for 24 hours.

Figure 1:
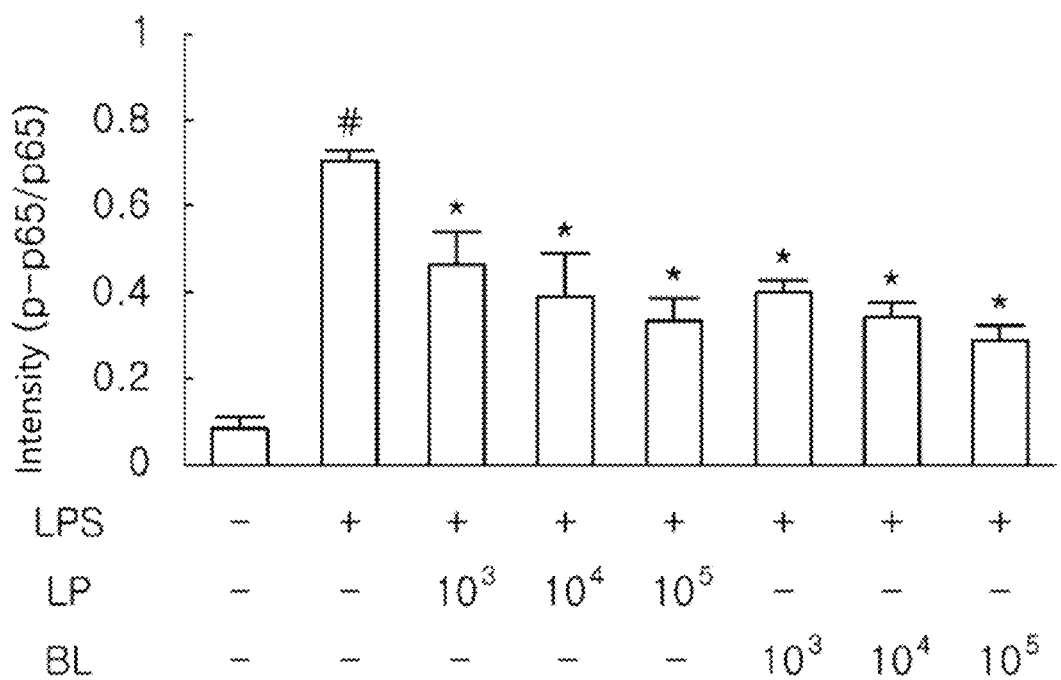
FIG. 1 is a graph showing inhibitory capacity of *Lactobacillus plantarum* NK3 and *Bifidobacterium longum* NK49, which are novel lactic acid bacteria, against an activity of NF-kB (p-p65/p65) to macrophage.
Figure 2:
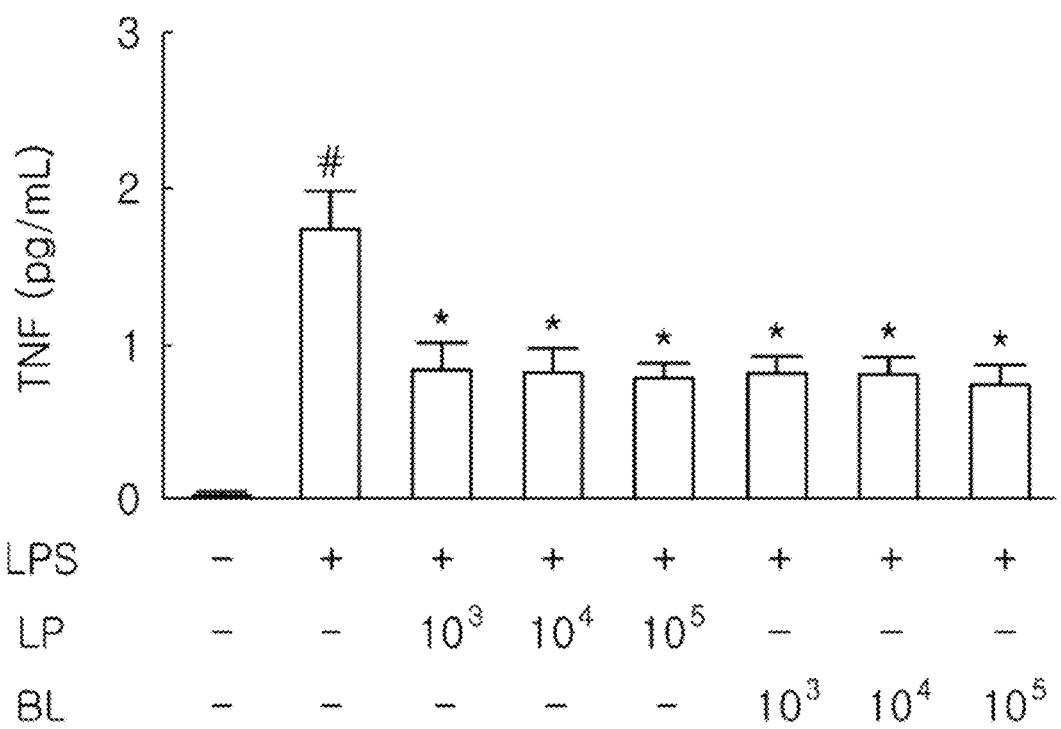
FIG. 2 is a graph showing inhibitory capacity of *Lactobacillus plantarum* NK3 and *Bifidobacterium longum* NK49, which are novel lactic acid bacteria, against an expression level of TNF-α to macrophage.

In result, it was identified that an activity of NF-kB is inhibited and an expression level of TNF-α is inhibited in all the groups treated with *Lactobacillus plantarum* NK3 or *Bifidobacterium longum* NK49 (FIGS. 1 and 2).

Example 4: Antibacterial Activity Against Vaginitis-Causing Bacteria (1) Antibacterial Test of Lactic Acid Bacteria

*Lactobacillus plantarum* NK3 and *Bifidobacterium longum* NK49 ($1 \times 10^6$, $1 \times 10^7$, $1 \times 10^8$ CFU/mL), which were the isolated novel lactic acid bacteria, were transplanted into GAM medium along with *Gardnerella vaginalis* or *Atopobium vaginae* ($1 \times 10^6$ CFU/mL). Culture was performed for 24 hours at 37° C. under an anaerobic condition in BHIS medium, in which yeast extract (1%), maltose (0.1%), glucose (0.1%) and horse serum (10%) were added into BHI broth, such that antibacterial activity was measured.

Figure 3:
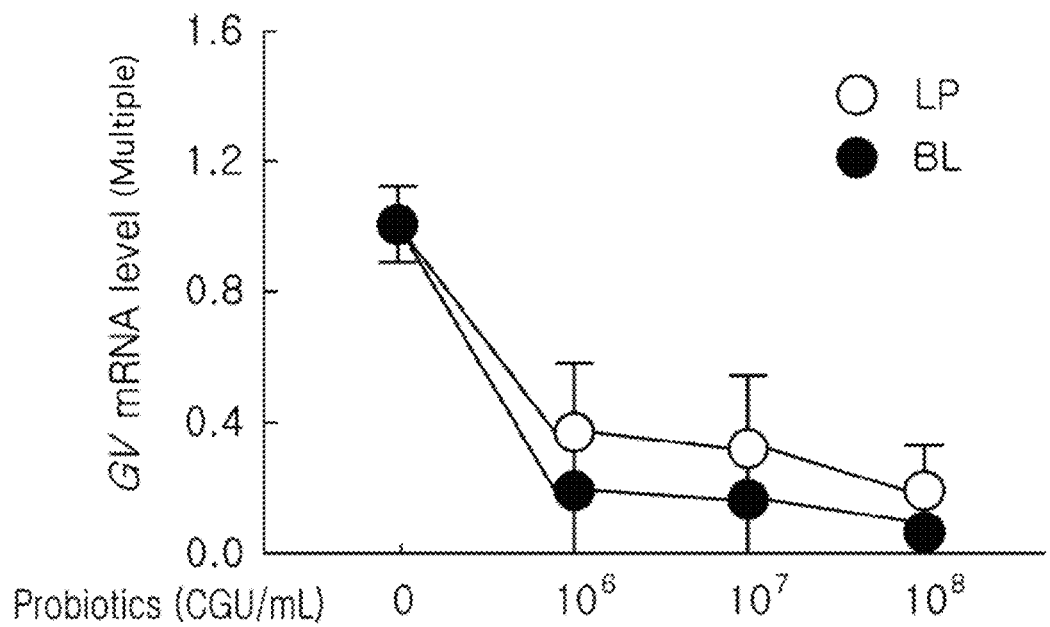
FIG. 3 is a graph showing an antibacterial effect of *Lactobacillus plantarum* NK3 and *Bifidobacterium longum* NK49, which are novel lactic acid bacteria, against *Gardnerella vaginalis*.
Figure 4:
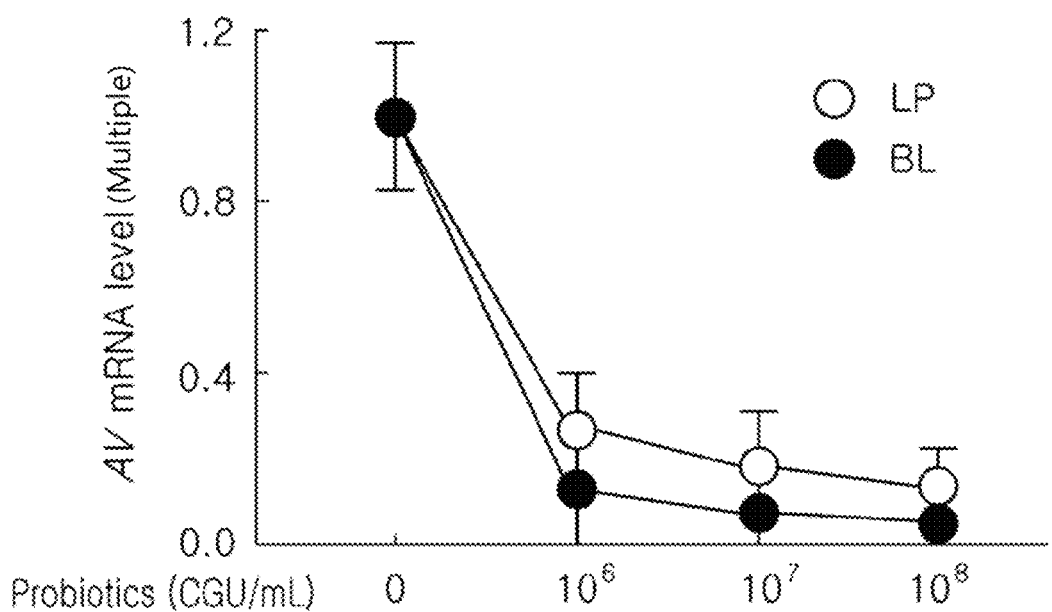
FIG. 4 is a graph showing an antibacterial effect of *Lactobacillus plantarum* NK3 and *Bifidobacterium longum* NK49, which are novel lactic acid bacteria, against *Atopobium vaginae*.

In result, it was identified that both *Lactobacillus plantarum* NK3 and *Bifidobacterium longum* NK49 show an effect of inhibiting growth of *Gardnerella vaginalis* and *Atopobium vaginae* by 95% or more (FIGS. 3 and 4).

(2) Infection Inhibitory Capacity of Lactic Acid Bacteria

While HeLa cells, which are a human cervical cancer cell line, were cultured in RPMI 1640 medium (containing 10% heat-inactivated fetal calf serum) at 37° C., 5% CO2 and 95% air conditions, *Lactobacillus plantarum* NK3 and *Bifidobacterium longum* NK49 ($1 \times 10^4$, $1 \times 10^6$ CFU/mL), which were the isolated lactic acid bacteria, were transplanted thereinto alone or in combination with said lactic acid bacteria ($1 \times 10^5$, $1 \times 10^6$, $1 \times 10^7$ CFU/mL) as well as *Gardnerella vaginalis* ($1 \times 10^5$ CFU/mL), such that the number of bacteria attached to the HeLa cells was measured through qPCR in 24 hours later.

Figure 5:
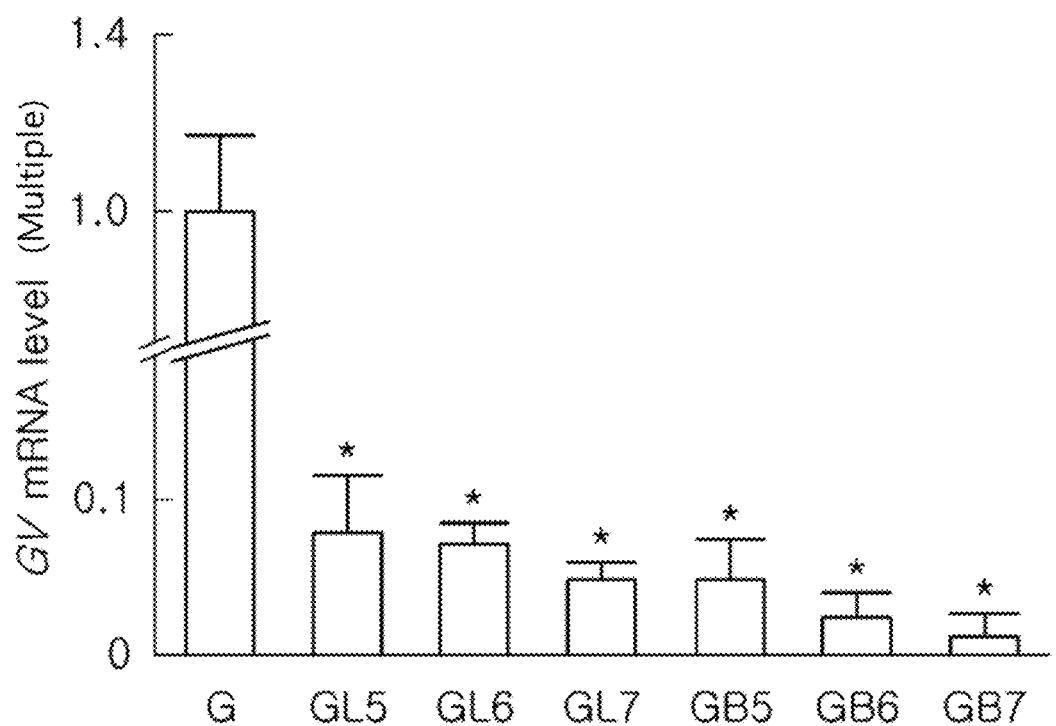
FIG. 5 is a graph showing an inhibitory capacity of *Lactobacillus plantarum* NK3 and *Bifidobacterium longum* NK49, which are novel lactic acid bacteria, against infection with *Gardnerella vaginalis*.

In result, it was identified that the number of *Gardnerella vaginalis* attached is remarkably decreased in the HeLa cells, into which *Lactobacillus plantarum* NK3 or *Bifidobacterium longum* NK49 was transplanted together (FIG. 5).

From the above experimental results, it can be understood that the novel lactic acid bacteria show not only an effect of inhibiting the growth of vaginitis-inducing bacteria, but also an effect of inhibiting infection with bacteria.

Example 5: Effect of Lactic Acid Bacteria on Treating Vaginitis in Animal Model (1) Preparation of Animal Model with Vaginitis and Administration of Lactic Acid Bacteria An experiment was performed by using six C57BL/6 mice (female, 19-22 g and 6 weeks old) per group. 0.125 mg of β-estradiol 17-benzoate (Sigma Inc., MO, USA) was dissolved in olive oil and subcutaneously injected into each of said mice. Three days later, *Gardnerella vaginalis* ($1 \times 10^8$ CFU/mouse) was transplanted into the vagina of the mouse. *Lactobacillus plantarum* NK3, *Bifidobacterium longum* NK49 or a 1:1 mixture thereof, which was the isolated novel lactic acid bacteria, was administered orally into the mouse or directly into the vagina thereof at $1 \times 10^9$ CFU/mouse once every day for 14 days from the 8th day after transplantation. The last administration was performed on the 7th day after the administration of lactic acid bacteria (14th day after transplantation), and an animal model was sacrificed in 24 hours later to perform an experiment.

(2) Identification of Occurrence of Intravaginal Inflammations

As a result of transplanting *Gardnerella vaginalis* into the vagina of the mouse as above, an inflammation with edema occurred to the vagina and the uterus. However, as a result of orally or intravaginally administering *Lactobacillus plantarum* NK3, *Bifidobacterium longum* NK49 or a mixture thereof, which is a novel lactic acid bacterium, it was identified that inflammations are significantly decreased in appearance in the vagina and the uterus (FIG. 6).

(3) Quantification of Lactic Acid Bacteria and *Gardnerella vaginalis* Strains

After administering the novel lactic acid bacteria as above, the inside of the vagina was washed with 0.5 ml of sterilized saline solution in 24 and 48 hours later. A resultant vaginal wash liquid was isolated with Qaigen DNA purification kit, after which lactic acid bacteria and *Gardnerella vaginalis* strains were quantified through PCR.

In result, it was identified that the number of infectious *Gardnerella vaginalis* bacteria is decreased by 99% or more in the group orally or intravaginally dosed with *Lactobacillus plantarum* NK3, *Bifidobacterium longum* NK49 or a mixture thereof (FIG. 7).

(4) Measurement of Myeloperoxidase Activity

A vaginal wash liquid obtained as above was added into 1 mL of 50 mM phosphate buffer (pH 6.0) and subjected to supersonic treatment. A process of thawing and freezing was performed three times, followed by centrifugation. 398 μL of o-dianisidine (0.129 mg/mL) was added into 100 μL of supernatant. A final concentration of $H_2O_2$ was set to 0.0005%, after which activity of myeloperoxidase (MPO) was measured at 25° C. and at 492 nm during time course.

In result, in case of the group infected with *Gardnerella vaginalis*, the activity of myeloperoxidase, which is a representative inflammation indicator of the vagina, was significantly increased. In case of the group orally or intravaginally dosed with *Lactobacillus plantarum* NK3, *Bifidobacterium longum* NK49 or a mixture thereof, however, it was identified that the activity of myeloperoxidase is remarkably decreased (FIG. 8).

(5) Analysis of Transcription Factors and Cytokines in Vaginal Mucosa

Lysis buffer (20 mM HEPES, 1.5 mM MgCl2, 0.4 mM NaCl, 1 mM EDTA, 1 mM dithiotheitol, 0.5 mM phenyl methyl sulfonyl fluoride, 20 μg/mL trypsin inhibitor, 1% NONIDET P-40, 20% glycerol) was injected into the colon or vaginal mucosa tissues of the animal model sacrificed above and was homogenized. A specimen was prepared to contain 50 μg/μL of proteins by quantifying the proteins with Bradford assay. 10 μg/4 of electrophoretic sample buffer (Laemmli sample buffer 950 μL+βMe 50 μL) was added into the specimen and denatured at 100° C. for three minutes to carry out electrophoresis (150 V, 30 mA). The electrophoresed gel was transferred to a membrane at 30 V for two hours. Said membrane was inserted into 5% skim milk/PBS-T (0.05% TWEEN 20/PBS) in an amount of 15 ml and shaken for one hour. 10 mL of 1% skim milk/PBS-T was inserted into 10 μg/μL of primary antibodies, then subjected to reaction for 12 hours, and then washed with PBS-T solution for five minutes three times. And, 20 mL of 1% skim milk/PBS-T was inserted into 10 μg/μL of secondary antibodies with regard to each of cytokines and transcription factors, and then subjected to reaction by shaking for one hour. Washing was performed with PBS-T solution for five minutes three times and ECL solution was subjected to luminescence at last.

In result, in case of the group infected with *Gardnerella vaginalis*, an expression of TNF-α was increased and an expression of IL-10 was decreased in vaginal tissues. However, in case of the group orally or intravaginally dosed with *Lactobacillus plantarum* NK3, *Bifidobacterium longum* NK49 or a mixture thereof, it was identified that an expression of TNF-α is inhibited and an expression of IL-10 is increased (FIGS. 9 and 10).

(6) Increase in Intravaginal Lactic Acid Bacteria

The inside of the vagina of the mouse was washed twice with 0.5 ml of sterilized saline solution. A resultant vaginal wash liquid was collected and centrifuged (10,000 g, 10 minutes), and DNA was extracted from precipitates by using a bacterial genomic DNA extraction kit (QIAGEN DNeasy Feces kit; Qiagen, Hilden, Germany). 10 ng of the extracted DNA was inserted into Qiagen thermal cycler and the following primers and SYBER premix were inserted thereinto, after which PCR was performed by carrying out DNA polymerase activation (95° C., 30 seconds), denaturation (95° C., 5 seconds) and amplification (63° C., 30 seconds) 38 times.

```
Lactobacilli forward (5'-3')
                                    (SEQ ID NO: 3)
CTC AAA ACT AAA CAA AGT TTC;

Lactobacilli reverse (5'-3')
                                    (SEQ ID NO: 4)
CTT GTA CAC ACC GCC CGT;

Control 16S rDNA forward (5'-3')
                                    (SEQ ID NO: 5)
AGA GTT TGA TCC TGG CTC AG;
and Control 16S rDNA reverse (5'-3')
                                    (SEQ ID NO: 6)
AAG GAG GTG WTC CAR CC.
```

In result, in case of being infected with *Gardnerella vaginalis*, it was identified that Lactobacilli are remarkably decreased. On the other hand, in case of being orally or intravaginally dosed with *Lactobacillus plantarum* NK3, *Bifidobacterium longum* NK49 or a mixture thereof, it was identified that said Lactobacilli are increased (FIG. 11). It means that Lactobacilli, which are decreased due to vaginitis induced by *Gardnerella vaginalis*, are recovered by the administration of said lactic acid bacteria, so as to restore acidic conditions inside the vagina.

From the above experimental results, it was identified that the novel lactic acid bacteria have an effect on preventing and treating vaginitis.

Example 5: Therapeutic Effect of Lactic Acid Bacteria on Colitis in Animal Model (1) Preparation of Animal Model with Colitis and Administration of Lactic Acid Bacteria An experiment was performed by using six C57BL/6 mice (male, 21-23 g and 6 weeks old) per group after being acclimated in a laboratory for one week. One group was a normal group and the mice in the rest of the groups were induced to develop colitis with 2,4,6-trinitrobenzenesulfonic acid (TNBS). Particularly, the experimental animals were anesthetized with ether, after which 0.1 ml of TNBS solution mixed in 50% ethanol was rectally administered into each colon of animals by using a 1 ml syringe with a round top, and then the animals were vertically lifted and maintained for 30 seconds to induce inflammations therefrom. On the other hand, the normal group was orally dosed with 0.1 ml of saline solution. *Lactobacillus plantarum* NK3, *Bifidobacterium longum* NK49 or a 1:1 mixture thereof, which is a novel lactic acid bacterium, was suspended in saline solution and orally administered in an amount of $1\times10^9$ CFU once daily for three days starting from the following day after administration. On the next day after finishing the administration of lactic acid bacteria, the experimental animals were sacrificed, after which a colon ranging from appendix to a region right before anus was removed from a large intestine and a length thereof was measured. After that, the following various indicators were identified from the above. On the other hand, the experimental animals of the normal group were orally dosed with 1% dextrose solution, which was suspension of lactic acid bacteria, instead of the novel lactic acid bacteria. Also, the experimental animals of the positive control group were orally dosed with 50 mg/kg of Sulfasalazine, which was a therapeutic drug for colitis, instead of the novel lactic acid bacteria.

(2) Measurement of Myeloperoxidase Activity

200 μl of 10 mM potassium phosphate buffer (pH 7.0) containing 0.5% hexadecyl trimethyl ammonium bromide was put into 100 mg of colon tissues, and subjected to homogenization. A resulting product was centrifuged at 4° C. and at 10,000 g for 10 minutes, so as to obtain a supernatant therefrom. 50 μl of the supernatant was put into 0.95 ml of a reaction solution (containing 1.6 mM tetramethyl benzidine and 0.1 mM $H_2O_2$), and then subjected to reaction at 37° C. so as to microscopically measure an observance at 650 nm. An activity of said myeloperoxidase was calculated with a resulting reactant $H_2O_2$ 1 μmol/ml=1 unit.

(3) Measurement of Inflammatory Indicators

Inflammatory reaction indicator materials such as p-p65, p65, COX-2 and β-actin were measured by using a western blotting method. Particularly, 50 μg of supernatant, which had been obtained by the same method as shown in an experiment for measuring the activity of said myeloperoxidase (MPO), was taken and subjected to immunoblotting. Also, an expression level of cytokines (IL-17 and TNF-α) was measured by using ELISA kit.

(4) Experimental Results

The experimental results performed as above are the same as shown in a following table 6.

TABLE 6

| Experimental group | Weight change g | Colon length cm | MPO activity μU/mg | TNF-α pg/mg | IL-17 pg/mg | NF-kB activity p-p65/p65 | COX-2 activity |
|---|---|---|---|---|---|---|---|
| Normal group | 0.9 | 6.5 | 0.21 | 35 | 17 | 0.12 | 0.23 |
| Induced group | −1.9 | 4.4 | 1.86 | 265 | 89 | 0.32 | 0.52 |
| LP NK3 | −0.9 | 5.2 | 1.12 | 89 | 45 | 0.23 | 0.35 |
| BL NK49 | −0.7 | 5.4 | 0.87 | 95 | 38 | 0.22 | 0.36 |

TABLE 6-continued

| Experimental group | Weight change g | Colon length cm | MPO activity µU/mg | TNF-α pg/mg | IL-17 pg/mg | NF-kB activity p-p65/p65 | COX-2 activity |
|---|---|---|---|---|---|---|---|
| Mixture | −0.7 | 5.5 | 0.82 | 88 | 35 | 0.19 | 0.29 |
| Positive control group | −1.0 | 5.1 | 1.26 | 105 | 47 | 0.25 | 0.42 |

Particularly, it was identified that there is no great change in weight of the group dosed with *Lactobacillus plantarum* NK3, *Bifidobacterium longum* NK49 or a mixture thereof, thereby showing no toxicity. Also, when inducing colitis, a length of colon was decreased. However, in case of the group dosed with lactic acid bacteria, it was identified that there occurs an effect of recovering a length of colon. Furthermore, in case of the group dosed with lactic acid bacteria, it was identified that an activity of myeloperoxidase, which is increased according to induced colitis, is decreased, an expression level of TNF-α and IL-17 cytokines is inhibited, and activities of NF-kB and COX-2 are inhibited.

From the results, it was identified that the novel lactic acid bacteria have an effect of preventing and treating colitis, without showing any toxicity.

Accession Information of Lactic Acid Bacteria

The present inventors deposited *Lactobacillus plantarum* NK3 for the purpose of patent to the Korean Culture Center of Microorganisms, a certified depository institution (address: Yulim Building, 45, Hongjenae 2ga-gil, Seodaemun-gu, Seoul, South Korea) on Aug. 4, 2017, and received an accession number of KCCM12089P.

Also, the present inventors deposited *Bifidobacterium longum* NK49 for the purpose of patent to the Korean Culture Center of Microorganisms, a certified depository institution (address: Yulim Building, 45, Hongjenae 2ga-gil, Seodaemun-gu, Seoul, South Korea) on Aug. 4, 2017, and received an accession number of KCCM12088P.

BUDAPEST TREATY ON THE INTERNATIONAL
RECOGNITION OF THE DEPOSIT OF MICROORGANISMS
FOR THE PURPOSES OF PATENT PROCEDURE
INTERNATIONAL FORM

| To. KIM DONG HYUN 26, Kyungheedae-ro, Dongdaemun-gu, Seoul, 02447, Republic of Korea | RECEIPT IN THE CASE OF AN ORIGINAL issued pursuant to Rule 7.1 by the INTERNATIONAL DEPOSITARY AUTHORITY identified at the bottom of this page |
|---|---|

I. IDENTIFICATION OF THE MICROORGANISM

| Identification reference given by the DEPOSITOR: Bifidobacterium longum NK49 | Accession number given by the INTERNATIONAL DEPOSITARY AUTHORITY: KCCM12088P |
|---|---|

II. SCIENTIFIC DESCRIPTION AND/OR PROPOSED TAXONOMIC DESIGNATION

The microorganism identified under I above was accompanied by:
[ ] a scientific description
[ ] a proposed taxonomic designation
(Mark with a cross where applicable)

III. RECEIPT AND ACCEPTANCE

This International Depositary Authority accepts the microorganism identified under I above, which was received by it on August. 04. 2017. (date of the original deposit)[1]

IV. INTERNATIONAL DEPOSITARY AUTHORITY

| Name : Korean Culture Center of Microorganism Address: Yurim B/D 45, Hongjenae-2ga-gil Seodaemun-gu SEOUL 120-861 Republic of Korea | Signature(s) of person(s) having the power to represent the International Depositary Authority or of authorized official(s): Date: August. 04. 2017. |
|---|---|

[1]Were Rule 6.4(d) applies, such date is the date on which the status of international depositary authority was acquired: where a deposit made outside the Budapest Treaty after the acquisition of the status of international depositary authority is converted into a deposit under the Budapest Treaty, such date is the date on which the microorganism was received by the international depositary authority.

BUDAPEST TREATY ON THE INTERNATIONAL
RECOGNITION OF THE DEPOSIT OF MICROORGANISMS
FOR THE PURPOSES OF PATENT PROCEDURE
INTERNATIONAL FORM

| To. KIM DONG HYUN<br>26, Kyungheedae-ro,<br>Dongdaemun-gu,<br>Seoul, 02447,<br>Republic of Korea | RECEIPT IN THE CASE OF AN ORIGINAL<br>issued pursuant to Rule 7.1 by the<br>INTERNATIONAL DEPOSITARY AUTHORITY<br>identified at the bottom of this page |
|---|---|

I. IDENTIFICATION OF THE MICROORGANISM

| Identification reference given by the<br>DEPOSITOR:<br>Bifidobacterium longum NK3 | Accession number given by the<br>INTERNATIONAL DEPOSITARY AUTHORITY:<br>KCCM12089P |
|---|---|

II. SCIENTIFIC DESCRIPTION AND/OR PROPOSED TAXONOMIC DESIGNATION

The microorganism identified under I above was accompanied by:
[ ] a scientific description
[ ] a proposed taxonomic designation
(Mark with a cross where applicable)

III. RECEIPT AND ACCEPTANCE

This International Depositary Authority accepts the microorganism identified under I above, which was received by it on August. 04. 2017. (date of the original deposit)[1]

IV. INTERNATIONAL DEPOSITARY AUTHORITY

| Name : Korean Culture Center of<br>Microorganism<br>Address: Yurim B/D<br>  45, Hongjenae-2ga-gil<br>  Seodaemun-gu<br>  SEOUL 120-861<br>  Republic of Korea | Signature(s) of person(s) having the<br>power<br>to represent the International Depositary<br>Authority or of authorized official(s):<br>Date: August. 04. 2017. |
|---|---|

[1]Were Rule 6.4(d) applies, such date is the date on which the status of international depositary authority was acquired: where a deposit made outside the Budapest Treaty after the acquisition of the status of international depositary authority is converted into a deposit under the Budapest Treaty, such date is the date on which the microorganism was received by the international depositary authority.

The invention claimed is:

1. A method of treating an inflammatory disease comprising administering to a mammalian subject having a symptom of the disease an effective amount of *Bifidobacterium longum* NK49 having the accession number KCCM12088P, wherein said inflammatory disease is colitis or vaginitis.

2. The method of claim 1, wherein the method further comprises administering an effective amount of *Lactobacillus plantarum* NK3 having the accession number KCCM12089P.

3. The method of claim 1, wherein the *Bifidobacterium longum* NK49 having the accession number KCCM12088P comprises the 16S rDNA sequence of SEQ ID NO: 2.

4. The method of claim 2, wherein the *Lactobacillus plantarum* NK3 having the accession number KCCM12089P comprises the 16S rDNA sequence of SEQ ID NO: 1.

5. The method of claim 1, wherein the *Bifidobacterium longum* NK49 having the accession number KCCM12088P is a live bacterial cell thereof or a dead bacterial cell thereof, a culture product thereof, a crushed product thereof or an extract thereof.

6. The method of claim 2, wherein the *Lactobacillus plantarum* NK3 having the accession number KCCM12089P is a live bacterial cell thereof or a dead bacterial cell thereof.

7. The method of claim 1, wherein the said inflammatory disease is colitis and said administering is oral administering.

8. The method of claim 1, wherein the said inflammatory disease is vaginitis and said administering is oral or intravaginal administering.

9. The method of claim 1, wherein the effective amount is $1 \times 10^2$ to $1 \times 10^{11}$ CFU/kg a day.

10. The method of claim 2, wherein the effective amount is $1 \times 10^2$ to $1 \times 10^{11}$ CFU/kg a day.

* * * * *

SEQUENCE LISTING

<160> NUMBER OF SEQ ID NOS: 6

<210> SEQ ID NO 1
<211> LENGTH: 1436
<212> TYPE: DNA
<213> ORGANISM: Artificial Sequence
<220> FEATURE:
<223> OTHER INFORMATION: NK3 16s rDNA

<400> SEQUENCE: 1

```
gcaagtcgaa cgaactctgg tattgattgg tgcttgcatc atgatttaca tttgagtgag      60
tggcgaactg gtgagtaaca cgtgggaaac ctgcccagaa gcgggggata acacctggaa     120
acagatgcta ataccgcata acaacttgga ccgcatggtc cgagcttgaa agatggcttc     180
ggctatcact tttggatggt cccgcggcgt attagctaga tggtgggta atggctcacc      240 atggcaatga tacgtagccg acctgagagg gtaatcggcc acattgggac tgagacacgg     300
cccaaactcc tacgggaggc agcagtaggg aatcttccac aatggacgaa agtctgatgg     360
agcaacgccg cgtgagtgaa gaagggtttc ggctcgtaaa actctgttgt taagaagaa     420 catatctgag agtaactgtt caggtattga cggtatttaa ccagaaagcc acggctaact     480
acgtgccagc agccgcggta atacgtaggt ggcaagcgtt gtccggattt attgggcgta    540
aagcgagcgc aggcggtttt ttaagtctga tgtgaaagcc tttcggctca accgaagaag    600
tgcatcggaa actgggaaac ttgagtgcag aagaggacag tggaactcca tgtgtagcgg    660
```

```
tgaaatgcgt agatatatgg aagaacacca gtggcgaagg cggctgtctg gtctgtaact      720
gacgctgagg ctcgaaagta tgggtagcaa acaggattag ataccctggt agtccatacc      780
gtaaacgatg aatgctaagt gttggagggt ttccgccctt cagtgctgca gctaacgcat      840
taagcattcc gcctggggag tacggccgca aggctgaaac tcaaaggaat tgacggggc       900 ccgcacaagc ggtggagcat gtggtttaat tcgaagctac gcgaagaacc ttaccaggtc      960
ttgacatact atgcaaatct aagagattag acgttccctt cggggacatg gatacaggtg     1020
gtgcatggtt gtcgtcagct cgtgtcgtga gatgttgggt taagtcccgc aacgagcgca     1080
acccttatta tcagttgcca gcattaagtt gggcactctg gtgagactgc cggtgacaaa     1140
ccggaggaag gtggggatga cgtcaaatca tcatgcccct tatgacctgg gctacacacg     1200
tgctacaatg gatggtacaa cgagttgcga actcgcgaga gtaagctaat ctcttaaagc     1260
cattctcagt tcggattgta ggctgcaact cgcctacatg aagtcggaat cgctagtaat     1320
cgcggatcag catgccgcgg tgaatacgtt cccgggcctt gtacacaccg cccgtcacac     1380
catgagagtt tgtaacaccc aaagtcggtg ggtaacctt ttaggaacca gccgcc          1436
```

<210> SEQ ID NO 2
<211> LENGTH: 1342
<212> TYPE: DNA
<213> ORGANISM: Artificial Sequence
<220> FEATURE:
<223> OTHER INFORMATION: NK49 16s rDNA

<400> SEQUENCE: 2

```
ggctttgctt ggtggtgaga gtggcgaacg ggtgagtaat gcgtgaccga cctgccccat       60
acaccggaat agctcctgga aacgggtggt aatgccggat gctccagttg atcgcatggt      120
cttctgggaa agctttcgcg gtatgggatg gggtcgcgtc ctatcagctt gacggcgggg      180
taacggccca ccgtggcttc gacgggtagc cggcctgaga gggcgaccgg ccacattggg      240
actgagatac ggcccagact cctacgggag gcagcagtgg ggaatattgc acaatgggcg      300
caagcctgat gcagcgacgc cgcgtgaggg atggaggcct cgggttgta aacctctttt       360 atcggggagc aagcgagagt gagtttaccc gttgaataag caccggctaa ctacgtgcca      420
gcagccgcgg taatacgtag ggtgcaagcg ttatcccgga attattgggc gtaaagggct      480
cgtaggcggt tcgtcgcgtc cggtgtgaaa gtccatcgct taacggtgga tccgcgccgg      540
gtacgggcgg gcttgagtgc ggtaggggag actggaattc ccggtgtaac ggtggaatgt      600
gtagatatcg gaagaacacc caatggcgaa ggcaggtctc tgggccgtta ctgacgctga      660
ggagcgaaag cgtggggagc gaacaggatt agataccctg gtagtccacg ccgtaaacgg      720
tggatgctat atgtggggcc cgttccacgg gttccgtgtc ggagctaacg cgttaagcat      780
cccgcctggg ggagtacggc cgcaaggcta aaactcaaag aaattgacgg gggcccgcac      840
aagcggcgga gcatgcggat taattcgatg caacgcgaag aaccttacct gggcttgaca      900
tgttcccgac ggtcgtagag atacggcttc ccttcggggc gggttcacag gtggtgcatg      960
gtcgtcgtca gctcgtgtcg tgagatgttg ggttaagtcc cgcaacgagc gcaaccctcg     1020
ccccgtgttg ccagcggatt atgccgggaa ctcacggggg accgccgggg ttaactcgga     1080
ggaaggtggg gatgacgtca gatcatcatg ccccttacgt ccagggcttc acgcatgcta     1140
caatggccgg tacaacggga tgcgacgcgg cgacgcggag cggatccctg aaaaccggtc     1200
tcagttcgga tcgcagtctg caactcgact gcgtgaaggc ggagtcgcta gtaatcgcga     1260
```

-continued

```
atcagcaacg tcgcggtgaa tgcgttcccg ggccttgtac acaccgcccg tcaagtcatg    1320
aaagtgggca gcacccgaag cc                                              1342

<210> SEQ ID NO 3
<211> LENGTH: 21
<212> TYPE: DNA
<213> ORGANISM: Artificial Sequence
<220> FEATURE:
<223> OTHER INFORMATION: Lactobacilli forward

<400> SEQUENCE: 3
ctcaaaacta aacaaagttt c                                               21

<210> SEQ ID NO 4
<211> LENGTH: 18
<212> TYPE: DNA
<213> ORGANISM: Artificial Sequence
<220> FEATURE:
<223> OTHER INFORMATION: Lactobacilli reverse

<400> SEQUENCE: 4
cttgtacaca ccgcccgt                                                   18

<210> SEQ ID NO 5
<211> LENGTH: 20
<212> TYPE: DNA
<213> ORGANISM: Artificial Sequence
<220> FEATURE:
<223> OTHER INFORMATION: Control 16S rDNA forward

<400> SEQUENCE: 5
agagtttgat cctggctcag                                                 20

<210> SEQ ID NO 6
<211> LENGTH: 17
<212> TYPE: DNA
<213> ORGANISM: Artificial Sequence
<220> FEATURE:
<223> OTHER INFORMATION: Control 16S rDNA reverse

<400> SEQUENCE: 6
aaggaggtgw tccarcc                                                    17
```